United States Patent [19]
Chen et al.

[11] Patent Number: 6,020,299
[45] Date of Patent: Feb. 1, 2000

[54] SINGLE PHASE CLEANING FLUID

[75] Inventors: Hang-Chang Bobby Chen, Getzville; Mark E. Lindrose, Buffalo, both of N.Y.

[73] Assignee: Occidental Chemical Corporation, Dallas, Tex.

[21] Appl. No.: 08/329,940

[22] Filed: Oct. 27, 1994

[51] Int. Cl.[7] ............................... C11D 7/30; C11D 7/50; C23G 5/028

[52] U.S. Cl. .................... 510/412; 510/408; 510/409; 510/411; 134/40; 252/364

[58] Field of Search .................... 252/162, 170, 252/171, 172, 153, 364; 134/40; 510/408, 409, 411, 412

[56] References Cited

U.S. PATENT DOCUMENTS

| | | | |
|---|---|---|---|
| 3,871,975 | 3/1975 | Nagase et al. | 204/59 F |
| 3,882,193 | 5/1975 | Rice et al. | 260/874 |
| 3,957,672 | 5/1976 | Zisman et al. | 252/171 |
| 4,038,276 | 7/1977 | Geiger et al. | 260/248 C |
| 4,359,394 | 11/1982 | Gainer et al. | 252/54 |
| 4,401,871 | 8/1983 | Lloyd et al. | 252/570 |
| 4,578,209 | 3/1986 | Hisamoto et al. | 252/143 |
| 5,162,384 | 11/1992 | Owens et al. | 521/110 |
| 5,208,339 | 5/1993 | Fukaya et al. | 544/79 |
| 5,240,641 | 8/1993 | Rowe | 252/364 |
| 5,242,503 | 9/1993 | Rowe | 134/10 |
| 5,244,507 | 9/1993 | Rowe | 134/38 |
| 5,401,429 | 3/1995 | Flynn et al. | 252/171 |
| 5,403,514 | 4/1995 | Matsuhisa et al. | 252/364 |
| 5,535,925 | 7/1996 | Hinden et al. | 222/327 |
| 5,643,982 | 7/1997 | Liu | 524/267 |
| 5,730,894 | 3/1998 | Minor | 252/67 |
| 5,749,956 | 5/1998 | Fisher et al. | 106/287.28 |
| 5,756,002 | 5/1998 | Chen et al. | 252/364 |
| 5,840,998 | 11/1998 | Mandal et al. | 568/655 |

FOREIGN PATENT DOCUMENTS

| 465037 | 1/1992 | European Pat. Off. . |

OTHER PUBLICATIONS

Grant & Hackh's Chemical Dictionary, Fifth Edition, definition of "nitro–", no month available 1987.

Webster's Ninth New Collegiate Dictionary, definition of "nitro–", no month available 1986.

Chemical Abstracts listing of compounds having the formula C5F11NO, no month available 1999.

*Primary Examiner*—Christine Skane
*Attorney, Agent, or Firm*—Anne E. Brookes; Richard D. Fuerle

[57] ABSTRACT

Disclosed is a single phase mixture of about 1 to about 99 wt % of a compound having the general formula

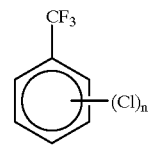

where "n" is 1 or 2 and about 0.1 to about 99 wt % of a liquid which can be a perfluoro aliphatic alkane from $C_5$ to $C_8$, a perfluoro cycloaliphatic alkane from $C_5$ to $C_8$, a perfluoro alkylcycloalkane having 5 to 8 carbon atoms in the ring and 1 or 2 branches of 1 to 3 carbon atoms each, a perfluoro-N-alkylmorpholine from $C_5$ to $C_8$, a perfluoro cycloether from $C_4$ to $C_7$, or a perfluoro polyether having an average molecular weight from about 400 to about 500.

20 Claims, No Drawings

SINGLE PHASE CLEANING FLUID

BACKGROUND OF THE INVENTION

This invention relates to a single phase mixture of a chlorinated benzotrifluoride and a perfluorinated liquid. In particular, it relates to a mixture of mono- or dichlorobenzotrifluoride with a perfluoro aliphatic or cycloaliphatic alkane, a perfluoroalkylcycloalkane, a perfluoro-N-alkylmorpholine, a perfluorocyclic ether, or a perfluoro polyether.

The solvents 1,1,1-trichloroethane and methylene dichloride have been used in a variety of industrial cleaning applications because they are good solvents for many organic compounds and lack a flashpoint under normal conditions of use, thereby providing a margin of fire safety to workers. While 1,1,1-trichloroethane evaporates quickly, it has been implicated in the destruction of stratospheric ozone. Regulations now limit its use and it may soon be prohibited entirely for many applications. Methylene chloride is also a highly effective cleaning solvent, but it has been classified as a possible carcinogen and is listed as a hazardous air pollutant. As a result, many companies are searching for alternative fluids that are not only effective cleaning solvents, but are non-flammable, are not ozone depleters, and are non-toxic and non-carcinogenic.

SUMMARY OF THE INVENTION

We have discovered a single phase fluid which is very effective at cleaning greases and soils from surfaces. The fluid is a mixture of a chlorinated benzotrifluoride compound and a perfluorinated liquid. This mixture displays several unusual and unexpected properties. First, the mixture is single phase only when the proportion of the perfluoro compound is very small or very large—when the proportions are in the middle range the fluids are not miscible.

Second, the mixtures are non-flammable when as little as 5% or less of the perfluorinated liquid is present. While parachlorobenzotrifluoride is a good cleaning solvent, evaporates fast, is non-toxic, and is not an ozone depleter, it has a flashpoint of 109° F. (43° C.), which means that it must be carefully handled, stored, and used. The perfluorinated liquids are non-flammable and evaporate rapidly, but do not clean as well as PCBTF and are much more expensive. We have found, however, that by using only a small amount of the perfluorinated liquid a non-flammable miscible mixture can be obtained which still retains the desirable properties of the chlorinated benzotrifluoride compound.

Several particular compositions also have unusual and unexpected properties. For example, when the perfluorinated liquid is $C_5F_{11}NO$, the composition is totally miscible in all proportions. Also, a mixture of $C_8F_{18}$ with parachlorobenoztrifluoride forms an azeotrope. That composition is not only non-flammable, but it can be recovered by distillation as the same composition.

DESCRIPTION OF THE PREFERRED EMBODIMENTS

The compositions of this invention are single phase mixtures of two components—a chlorinated benzotrifluoride and a perfluorinated liquid. The chlorinated benzotrifluoride has the formula

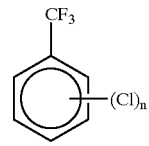

where "n" is 1 or 2 and is preferably 1 as monochlorobenzotrifluorides are more economical and have greater evaporation rates. The preferred dichlorobenzotrifluoride is 3,4-dichlorobenzotrifluoride (DCBTF) and the preferred monochlorobenzotrifluoride is parachlorobenzotrifluoride (PCBTF) as those compounds are commercially available. Also, while PCBTF is not a volatile organic compound (VOC), orthochlorobenzotrifluoride is a VOC.

The perfluorinated liquid is a compound in which hydrogen on carbon atoms has been replaced by fluorine. The perfluorinated liquid can be a perfluoro aliphatic alkane from $C_5$ to $C_8$, a perfluoro cycloaliphatic alkane from $C_5$ to $C_8$, a perfluoroalkylcycloalkane having 5 to 8 carbon atoms in the ring and 1 or 2 branches of 1 to 3 carbon atoms each, a perfluoro-N-alkylmorpholine from $C_5$ to $C_8$, a perfluorocyclic ether from $C_4$ to $C_7$, or a perfluoro polyether having an average molecular weight of about 400 to about 500. Preferably, the perfluoro compound is a perfluoro aliphatic or cycloaliphatic alkane from $C_6$ to $C_8$, a perfluoroalkylcycloalkane having 5 to 7 carbon atoms in the ring and 1 or 2 branches of 1 to 3 carbon atoms each, and which preferably has a single branch of 1 carbon atom, a perfluoro-N-alkylmorpholine from $C_5$ to $C_7$, a perfluorocyclic ether from $C_4$ to $C_6$, or a perfluoro polyether having an average molecular weight of 440 to 480. The preferred perfluorinated liquids have the formula $C_mF_{2m+1}X$ where X is F or NO and "m" is 5 to 8. Examples of particularly preferred perfluorinated liquids include $C_5F_{11}NO$, $C_6F_{14}$, $C_7F_{16}$, $C_8F_{18}$, and $CF_3[(O-CF(CF_3)-CF_2)_p(OCF_2)_q]OCF_3$ where "p" is 0 to 2 and "q" is 0 to 5 as those perfluorinated liquids are commercially available and work well.

The compositions of this invention comprise about 1 to about 99.9 wt % of the chlorinated benzotrifluoride compound and about 0.1 to about 99 wt % of the perfluorinated liquid. The preferred compositions comprise about 80 to about 99.9 wt % of the chlorinated benzotrifluoride compound and about 0.1 to about 20 wt % of the perfluorinated liquid as those mixtures are less expensive. The most preferred compositions comprise about 95 to about 99.9 wt % chlorinated benzotrifluoride and about 0.1 to about 5 wt % of the perfluorinated liquid. An azeotropic mixture that boils between 98 and 104° C. lies between about 1 to about 8 wt % parachlorobenzotrifluoride and about 92 to about 99 wt % $C_8F_{18}$. Compositions made with $C_5F_{11}NO$ are miscible in all proportions.

The compositions are easily prepared by simply mixing together the chlorinated benzotrifluoride compound and the perfluorinated liquid in a miscible proportion. The compositions can be used as hard surface cleaners for cleaning brakes, wires, cables, aircraft, carburators, engines, and the like, or for cold cleaning of work pieces, such as dip cleaning, vapor degreasing replacement, or refrigeration system cleaning. The compositions are also useful in cleaning circuit boards, electric motors, wafers, optics, bearings, and chips. They may have applications in paints and coatings, adhesives, sealants, caulks, paint removers, and as carriers for lubricants, pesticides, dyes, and inks.

The following examples further illustrate this invention.

EXAMPLE 1

Miscibility

Incremental amounts of various perfluorinated liquids were added to 20 grams PCBTF (sold by Occidental Chemical Corporation as "Oxsol®100") in a glass vial. After each addition, the mixtures were shaken and visually examined for miscibility. The additions were continued until a total of 20 grams of the perfluorinated liquid had been added to the PCBTF. The process was then reversed by adding incremental amounts of PCBTF to 20 grams of various perfluorinated liquids. The following table gives the perfluorinated liquids tested and the results.

| PERFLUORINATED LIQUID | WT % PERFLUORINATED LIQUID IN MISCIBLE MIXTURES WITH OXSOL ® 100 |
|---|---|
| $C_5F_{11}NO$ (sold by 3M as PF-5052) | 0–100 |
| $C_6F_{14}$ (sold by 3M as PF-5060) | 0–33 and 83–100 |
| $C_7F_{16}$ (sold by 3M as PF-5070) | 0–29 and 82–100 |
| $C_8F_{18}$ (sold by 3M as PF-5080) | 0–25 and 87–100 |
| Perfluorinated polyether (sold by Ausimont as Perfluorosolv ™ PFS-1)* | 0–11 and 91–100 |

*$CF_3[(O-CF(CF_3)CF_2)_p-(OCF_2)_q]-O-CF_3$ having an average molecular weight of 460.

These experiments show that only $C_5F_{11}NO$ is miscible in all proportions and that the other perfluorinated liquids are miscible at lower and higher concentrations.

EXAMPLE 2

Azeotrope

Batch distillations using a 10-tray Oldershaw distillation column were performed to determine whether any mixture of PCBTF with PF-5052, PF-5060, PF-5070, or PF-5080 were azeotropes. The distillation pot was charged with known amounts of PCBTF (Oxsol®100) and a perfluorinated liquid and the mixture was brought to a total reflux. Once a stable reflux rate had been established, distillate was removed from the reflux condenser. The distillate composition was determined by gas chromatography analyses.

For each binary mixture, two initial distillation operations were undertaken—one for 0.5 wt % of the perfluorinated liquid in 99.5 wt % PCBTF, and the other for 0.5 wt % PCBTF in 99.5 wt % of the perfluorinated liquid. If a distillate sample had a higher composition of the less volatile component than its starting material, an azeotrope existed somewhere within the chosen composition range. The composition range was then narrowed and the distillation procedure was repeated in order to more precisely identify that azeotropic composition. The only azeotrope found was between 1 and 8 wt % PCBTF and 92 and 99 wt % $C_8F_{18}$; it had an azeotropic temperature between 98° and 104° C.

EXAMPLE 3

Flash Point

Oxsol®100 was mixed with various perfluorinated liquids and the mixtures were tested for flash point using ASTM test D-5687, known as the Tag Closed Tester. The following table gives the results:

| PERFLUORINATED LIQUID IN OXSOL® 100 | TAG CLOSED CUP FLASH POINT (° F.) |
|---|---|
| — | 109 |
| 5 wt% PF-5052 | NFTB* |
| 5 wt% PF-5060 | NFTB |
| 5 wt% PF-5070 | NFTB |
| 5 wt% PF-5080 | NFTB |
| 5 wt% PFS-1 | NFTB |

-continued

| PERFLUORINATED LIQUID IN OXSOL® 100 | TAG CLOSED CUP FLASH POINT (° F.) |
|---|---|
| 3 wt% PF-5070 | NFTB |

(*No flash to boiling)

As a comparison, miscible mixtures of Oxsol®100 with perchloroethylene, a common non-flammable chemical, were prepared in various proportions and were tested using the same ASTM test. No elevation of the flash point of Oxsol®100 (109° F.) was found even for mixtures containing 50 wt % perchloroethylene.

We claim:

1. A composition which comprises a single phase mixture of (A) about 80 to about 99.9 wt % of a compound having the general formula

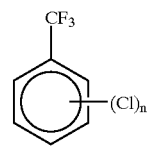

where "n" is 1 or 2; and (B) about 0.1 to about 20 wt % of a liquid selected from the group consisting of perfluoro aliphatic alkanes from $C_5$ to $C_8$, perfluoro cycloaliphatic alkanes from $C_5$ to $C_8$, perfluoroalkylcycloalkanes having 5 to 8 carbon atoms in the ring and 1 or 2 branches of 1 to 3 carbon atoms each, perfluoro-N-alkylmorpholines from $C_5$ to $C_8$, perfluoro cyclic ethers from $C_4$ to $C_7$, and perfluoro polyethers having an average molecular weight of about 400 to about 500.

2. A composition according to claim 1 in which the concentration of said liquid is sufficient to render said composition non-flammable.

3. A composition according to claim 1 wherein said compound is parachlorobenzotrifluoride.

4. A composition according to claim 1 wherein said liquid is at least 5 wt % of said composition.

5. A composition according to claim 1 wherein said liquid is a perfluoroaliphatic alkane from $C_6$ to $C_8$.

6. A composition according to claim 1 wherein said liquid is a perfluoro cycloaliphatic alkane from $C_6$ to $C_8$.

7. A composition according to claim 1 wherein said liquid is a perfluoroalkylcycloalkane having 5 to 7 carbon atoms in the ring and 1 or 2 branches of 1 to 3 carbon atoms each.

8. A composition according to claim 7 wherein said perfluoroalkylcycloalkane has 1 branch of 1 carbon atom.

9. A composition according to claim 1 wherein said liquid is a perfluoro-N-alkylmorpholine from $C_5$ to $C_7$.

10. A composition according to claim 1 wherein said liquid is a perfluorocyclic ether from $C_4$ to $C_6$.

11. A composition according to claim 1 wherein said liquid is a perfluoro polyether having an average molecular weight of 440 to 480.

12. A method of cleaning a substrate comprising contacting said substrate with a composition according to claim 1.

13. A composition which consists essentially of a single phase, non-flammable mixture of
    (A) about 80 to about 99.9 wt % parachlorobenzotrifluoride; and about 0.1 to about 20 wt % of a liquid perfluoro-N-alkylmorpholine from $C_5$ to $C_8$ or a liquid having the formula $C_mF_{2m+1}F$ or $CF_3[(O-CF(CF_3)-CF_2)_p-(OCF_2)_q]-OCF_3$, where "m" is 5 to 8, "p" is 0 to 2, and "q" is 0 to 5.

14. A single phase, non-flammable azeotropic mixture which consists essentially of about 1 to about 8 wt % parachlorobenzotrifluoride and about 92 to about 99 wt % $C_8F_{18}$.

15. A composition which comprises a single phase, non-flammable mixture of
    (A) about 95 to about 99.9 wt % parachlorobenzotrifluoride; and
    (B) about 0.1 to about 5 wt % of a liquid selected from the group consisting of perfluoro-N-methylmorpholine $C_6F_{14}$, $C_7F_{16}$, $C_8F_{18}$, and $CF_3[(O-CF(CF_3)-CF_2)_p(OCF_2)_q]OCF_3$ having an average molecular weight of about 400 to about 500, where "p" is 0 to 2 and "q" is 0 to 5.

16. A composition according to claim 15 wherein said liquid is perfluoro-N-methylmorpholine.

17. A composition according to claim 15 wherein said liquid is $C_6F_{14}$.

18. A composition according to claim 15 wherein said liquid is $C_7F_{16}$.

19. A composition according to claim 15 wherein said liquid is $C_8F_{18}$.

20. A composition according to claim 15 wherein said liquid is $CF_3[(O-CF(CF_3)-CF_2)_p-(OCF_2)_q]-OCF_3$, which has an average molecular weight of about 460.

* * * * *